United States Patent [19]

Gabillet

[11] Patent Number: 4,791,221

[45] Date of Patent: Dec. 13, 1988

[54] TRANSESTERIFICATION OF METHYL METHACRYLATE

[75] Inventor: Philippe Gabillet, Paris, France

[73] Assignee: Francaise d'Organo Synthese, Paris, France

[21] Appl. No.: 884,631

[22] Filed: Jul. 11, 1986

[30] Foreign Application Priority Data

Jul. 11, 1985 [FR] France ................. 85 10674

[51] Int. Cl.$^4$ ..................... C07C 67/02; C07C 67/48
[52] U.S. Cl. ..................... 560/217; 560/218
[58] Field of Search ................. 560/217, 218; 203/DIG. 21

[56] References Cited

U.S. PATENT DOCUMENTS 2,406,561  8/1946  Rehberg ................. 560/218
4,518,462  5/1985  Aoshima et al. ......... 560/218

FOREIGN PATENT DOCUMENTS 2744641  4/1979  Fed. Rep. of Germany ...... 560/217

OTHER PUBLICATIONS

Pedersen, C. J. et al., *Angew. Chem. Internat. Edit.*, vol. 11 (1972), pp. 16–25.

*Primary Examiner*—Paul J. Killos
*Attorney, Agent, or Firm*—Burns, Doane, Swecker & Mathis

[57] ABSTRACT

Methyl methacrylate is efficiently transesterified with a heavy alcohol in the presence of (i) defined amounts of a lithium catalyst incrementally added to the reaction medium, and (ii) an azeotrope-forming compound which forms, together with the methanol produced, an azeotrope distilling at a temperature of less than about 60° C.

8 Claims, No Drawings

TRANSESTERIFICATION OF METHYL METHACRYLATE

BACKGROUND OF THE INVENTION

1. Field of the Invention

The present invention relates to the preparation of methacrylic esters, and, more especially, to the preparation of such methacrylates by transesterification.

2. Description of the Prior Art

French Pat. No. 2,405,237 describes a process for the preparation of methacrylic esters by transesterification; it is stated therein that the process has been carried out in the presence of a transesterification catalyst, which consists of lithium hydroxide used in a proportion of 0.01 to 2% by weight with respect to the total weight of the reagents, as well as in the presence of a known methacrylate polymerization inhibitor. This '237 patent also notes that the reaction mixture is heated, under total reflux, until that point in time whereat the head of the column the temperature of the methyl methacrylate/methanol azeotrope is attained, such azeotrope enabling the gradual elimination of the methanol present in the reaction medium.

A systematic study of the transesterification of methyl methacrylate with higher alcohols, utilizing a lithium compound (preferably the hydroxide or carbonate) as the catalyst, has shown that it is possible and industrially attractive to only use amounts of catalyst less than those specified in said French Pat. No. 2,405,237, under such conditions that, on the one hand, the catalyst is gradually introduced into the reaction medium, and, on the other, the reaction is carried out in the presence of an inert azeotrope-forming compound which produces, with the methanol present in the reaction medium, an azeotrope boiling at a temperature of less than approximately 60° C. (at atmospheric pressure).

SUMMARY OF THE INVENTION

Accordingly, a major object of the present invention is the provision of an improved process for the transesterification of methyl methacrylate with a heavier alcohol, in the presence of a lithium catalyst and wherein the amount of the lithium catalyst employed ranges from 6 to 30 ppm (expressed as lithium) of lithium hydroxide or carbonate, the lithium catalyst is gradually added to the reaction medium, and the reaction is carried out in the presence of an azeotrope-former which gives rise, together with the methanol, to an azeotrope boiling at a temperature of less than approximately 60° C.

Consistent herewith, the amount of the catalyst is expressed relative to the total weight of the reagents, i.e., the sum of the weights of the methyl methacrylate and the alcohol.

DETAILED DESCRIPTION OF THE PREFERRED EMBODIMENTS OF THE INVENTION

More particularly, according to the present invention, and as would be apparent to one skilled in this art, the subject transesterification is advantageously carried out in the presence of a methacrylate polymerization inhibitor. Exemplary of such polymerization inhibitors, representative are hydroquinone monoethyl ether, hydroquinone, 2,6-di-t-butylpara-cresol, 3,5-di-t-butyl-4-hydroxyanisole, 2,5-di-t-butylhydroxyanisole, N,N'-dinaphthyl-para-phenylenediamine, and 2-t-butyl-4-methoxyphenol, together with any other radical polymerization inhibitor, the amounts of such inhibitors typically ranging from 100 to 1,400 ppm (by weight relative to the expected theoretical amount of the ester).

The alcohols that may be used for the transesterification of methyl methacrylate according to the invention are quite varied and numerous. The following are exemplary of such heavy alcohols: aliphatic linear or branched chain monoalcohols, such as n-butanol, n-propanol, lauryl alcohol, stearyl alcohol, 2-ethylhexanol; cycloaliphatic alcohols, such as cyclohexanol; aromatic alcohols, such as benzyl alcohol; alcohols bearing other functional groups, e.g., ethylene glycol monomethylether, ethylene glycol monoisopropylether; unsaturated alcohols, such as allyl alcohol; aliphatic polyols, such as monoethylene glycol, diethylene glycol, butanediol, trimethylol propane, with the transesterifying alcohols being either natural or synthetic in origin.

The catalyst used comprises lithium, advantageously in the form of lithia (calcined or monohydrate) or lithium carbonate.

As regards the azeotrope-former, any inert compound (for example, and preferably, a saturated hydrocarbon, such as hexane) producing an azeotrope with methanol and boiling at a temperature of less than about 60° C., may be used. In actual fact, the use of such azeotrope-former enables the elimination of the methanol present (or formed) in the reaction medium, but at the same time avoiding the formation of the methyl methacrylate/methanal azeotrope which evaporates at about 65° C.

Also, according to the present invention, the catalyst is gradually introduced into the reaction medium. In fact, the consumption of the catalyst by the reaction of the lithium with one of the reagents present must be prevented by maintaining the concentration of the catalyst at a very low level. The period of time during which the catalyst is introduced into the reaction medium varies with the experimental conditions and the kinetics of the reaction. Typically, the catalyst should be gradually introduced into the reaction medium over a period of from 1/10 to ½ of the overall period of reaction.

It has also been discovered, and this constitutes another object of the invention, that the catalytic activity of the lithium may be enhanced by the use of crown ethers and/or cryptants. Exemplary of such cocatalysts, the following are respresentative: 1,4,7,10-tetraoxocyclodecane (crown 2-4) or tris(3,6-dioxaheptyl)amine (TDA1); the amounts to be used, expressed in moles per mole of the $Li^+$ ion, advantageously range from 0.01 to 2 moles per mole. For further description of such cocatalysts, see U.S. Pat. No. 4,417,081.

The subject transesterification is preferably carried out in the following manner: the transesterifying alcohol, the polymerization inhibitor and an azeotrope-forming solvent are introduced and heated for that period of time required to dehydrate the reaction medium.

When the medium is sufficiently dehydrated and the temperature of the reaction mass ranges from 100° to 140° C., and after the residual acidities of the reagents have been neutralized, the methyl methacrylate and a methanolic solution of lithium hydroxide or a methanolic suspension of lithium carbonate are simultaneously introduced therein. The methanol formed is extracted from the reaction medium by azeotropic distillation under atmospheric pressure.

Air may be bubbled through the reaction medium to reinforce the effectiveness of the polymerization inhibitor. Similarly, the addition of the cryptants or crown ethers enhances the catalytic effect of the catalyst employed.

The compounds obtained according to the process of the invention are readily isolated in the following manner:

Subsequent to distillation under reduced pressure to eliminate, e.g., the hexane and the excess of light compounds, it is possible either to purify the product ester by distillation, if it has adequate volatility, or, contrariwise, it may be subjected to a specific treatment which narrowly depends upon the type of inhibitor used.

Treatment 1

This treatment is adapted for inhibitors of radical polymerization which contain a nitrogen atom. The treatment consists of passing the reaction product over acidic clay or charcoal, followed by filtration; the passage over acid clay may optionally be preceded by acidulation.

Treatment 2

This treatment is particularly suitable for inhibitors of radical polymerization of the quinone and phenol type and consists of passing the reaction product over basic clay or charcoal, followed by filtration; it may advantageously be preceded by basification.

In order to further illustrate the present invention and the advantages thereof, the following specific examples are given, it being understood that same are intended only as illustrative and in nowise limitative.

EXAMPLE 1

Into a 6 liter flask having seven necks, equipped with a thermometer, an agitator, a funnel for the introduction of hexane, a funnel for the introduction of the catalyst, a funnel for the introduction of methyl methacrylate, an air bubbler, and which was surmounted by a distillation column (internal diameter, 40 mm; height 1.50 m; 18 actual plates), a column head and a downstream condenser and a horizontal decanter, maintained at 10° C., and also containing a temperature sensor, an outlet for the bottom layer and means to recycle the top layer to the head of the column, the following materials were introduced: 1573 g stearyl alcohol (6 moles), 600 ml hexane and 1 g N,N'-dinaphthyl-para-phenylenediamine, 5.36 ml of a solution of 2.49% calcined lithium hydroxide in methanol. After drying for 45 min and when the column was in equilibrium, methyl methacrylate (690.9 g in 0 hr, 45 min) and a methanolic solution of lithia (10.24 ml in 1 hr, 30 min), were simultaneously poured therein.

The temperature of the reaction mass was maintained from 115° C. to 120° C. by the optional addition of hexane.

The heteroazeotrope was cooled to 10° C. such that the lower layer could be decanted. After a reaction time of 4 hr, a conversion yield of the alcohol of 98% was obtained.

EXAMPLE 2

The procedure of Example 1 was repeated, but the transesterifying alcohol was an isodecanol fraction (average molecular weight: 160.3 g). A conversion of 100% was obtained after 4 hours of reaction.

EXAMPLE 3

Into a 300 liter stainless steel reactor equipped in a manner similar to the 6 liter flask described in Example 1, the following materials were charged: 80 kg stearyl alcohol (average molecular weight: 262.15 g), 25 kg hexane and 50 g N,N'-dinaphthyl-para-phenylenediamine and 5.41 g lithium hydroxide monohydrate After the dehydration of the reaction medium, over 0 hr, 15 min, 36.6 kg methyl methacrylate (over 0 hr, 35 min) were simultaneously introduced therein. Following a reaction time of 5 hr, 5 g lithium hydroxide monohydrate dissolved in 200 g methanol were introduced. After a reaction time of 6 hr, the degree of conversion of the stearyl alcohol was 98.2% (determined by chromatography).

EXAMPLE 4

The procedure of Example 1 was repeated, but 0.021 g TDA1 (marketed by Rhone-Poulenc) were mixed into the methyl methacrylate to be introduced. After a reaction time of 4 hr, an alcohol conversion of 99.2% was obtained.

EXAMPLE 5

The procedure was similar to that of Example 1, but the transesterifying alcohol was a lauryl alcohol fraction having an average molecular weight of 207 g and the polymerization inhibitor was 2,6-di-t-butyl-para-cresol. After a 4 hr reaction, a conversion of 98.5% was obtained.

EXAMPLE 6

The procedure of Example 1 was repeated, but the transesterifying alcohol was a lauryl alcohol fraction having an average molecular weight of 207 g and the polymerization inhibitor was 2-t-butyl-4-methoxyphenol. After a reaction time of 4 hr, an alcohol conversion of 98.7% was obtained.

EXAMPLE 7

500 g crude stearyl methacrylate obtained as in Example 1 and containing 500 ppm N,N'-dinaphthyl-para-phenylenediamine, were introduced into a 1 liter five-necked flask, equipped with an agitator and surmounted by a direct condenser, a thermometer, an immersion device for air bubbling and means for the introduction of solids. The temperature of the reaction mass was raised to 80°–90° C. under agitation and air bubbling, after which 6 g Fulcat B were rapidly introduced. The temperature was then maintained at 80°–90° C. for 0 hr, 30 min, whereupon the reaction medium was cooled to 50° C. and filtered through a layer of DIC clarcel. 492 g stearyl methacrylate containing 75 ppm N,N'-dinaphthyl-para-phenylenediamine were obtained. The filter cake may advantageously be rinsed with hexane to recycle the polymerization inhibitor and the retained stearyl methacrylate.

EXAMPLE 8

The procedure of Example 6 was repeated, with 1242 g lauryl alcohol (6 moles), but the polymerization inhibitor was hydroquinone monomethylether (250 ppm relative to the reagents). After 3 hr, 30 min, a conversion of 98% was obtained.

The top fraction of the reaction medium was removed continuously under vacuum at 155°–165° C., 70 to 130 mm Hg, in an apparatus equipped with an agitator, a thermometer, an immersion device for bubbling air, a Claisen head and a condenser.

The reaction mass, the top fraction of which had been removed, was then treated in a 4 liter flask equipped with an agitator, a thermometer and a condenser; the temperature of the reaction mass was then raised to 65° C., 2.7 g sodium hydroxide and 1.5 g Norit D 10 charcoal were introduced, the temperature was maintained at 65° C. for 0 hr, 20 min, the medium was treated with 3 g sawdust and filtered on DIC.

1532 g lauryl methacrylate containing 50 ppm of hydroquinone monomethylether were obtained.

While the invention has been described in terms of various preferred embodiments, the skilled artisan wil appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of methacrylic ester, comprising transesterifying methyl methacrylate with an alcohol heavier than methanol, wherein from 6 to 30 ppm of a lithium catalyst is incrementally added to the medium during transesterification, and wherein transesterification is carried out in the presence of an azeotrope-forming compound which forms, together with the methanol of reaction, an azeotrope which distills at a temperature of less than about 60° C.

2. The process as defined by claim 1, wherein said lithium catalyst comprises lithia, lithium hydroxide or lithium carbonate.

3. The process as defined by claim 1, wherein said transesterification is carried out in the further presence of a methacrylate polymerization inhibitor.

4. The process as defined by claim 1, wherein said heavy alcohol comprises a linear or branched chain aliphatic monoalcohol, a cycloaliphatic alcohol, an aromatic alcohol, a functional alcohol, an unsaturated alcohol, or an analiphatic polyol.

5. The process as defined by claim 1, wherein said azeotrope-forming compound comprises a saturated hydrocarbon.

6. The process as defined by claim 5, said saturated hydrocarbon comprising hexane.

7. The process as defined by claim 1, wherein said lithium catalyst is incrementally added over a period of time of from 1/10 to ½ of the overall period of reaction.

8. The process as defined by claim 1, further comprising adding cocatalytically effective amounts of a crown ether or cryptant to the medium of transesterification.

* * * * *